(12) United States Patent
Flot

(10) Patent No.: US 6,323,461 B2
(45) Date of Patent: Nov. 27, 2001

(54) CLAMPS WITH SHAPE MEMORY

(75) Inventor: Francis Flot, Nancy (FR)

(73) Assignee: M.B.A., S.A., Vandoeuvre (FR)

( * ) Notice: Subject to any disclaimer, the term of this patent is extended or adjusted under 35 U.S.C. 154(b) by 0 days.

(21) Appl. No.: 09/820,411

(22) Filed: Mar. 29, 2001

Related U.S. Application Data

(62) Division of application No. 09/462,862, filed on Jan. 14, 2000, now Pat. No. 6,268,589.

(30) Foreign Application Priority Data

| May 15, 1998 | (FR) | 98 06341 |
| May 7, 1999 | (FR) | 99 06042 |

(51) Int. Cl.$^7$ ................ H05B 1/00; H05B 3/42
(52) U.S. Cl. ............... 219/229; 219/201; 219/227; 219/233; 606/219
(58) Field of Search .................. 219/227, 229, 219/233, 221, 225, 230, 231, 238, 240, 241, 243, 201; 606/67, 76, 78, 108, 194, 219; 128/833, 899; 227/19, 120, 129; 411/909; 148/402, 426, 312; 236/101 R

(56) References Cited

U.S. PATENT DOCUMENTS

| 3,174,851 | * | 3/1965 | Buehler et al. | 148/402 |
| 3,868,956 | | 3/1975 | Alfidi et al. | 606/194 |
| 4,485,816 | | 12/1984 | Krumme | 606/219 |
| 4,550,870 | | 11/1985 | Krumme et al. | 227/19 |
| 4,665,906 | | 5/1987 | Jervis | 606/78 |
| 4,890,613 | * | 1/1990 | Golden et al. | 606/220 |
| 5,067,957 | | 11/1991 | Jervis | 606/108 |
| 5,190,546 | | 3/1993 | Jervis | 606/78 |
| 5,597,378 | | 1/1997 | Jervis | 606/78 |

FOREIGN PATENT DOCUMENTS

| 2747911 | 10/1997 | (FR) . |
| WO9616603 | 6/1996 | (WO) . |

* cited by examiner

*Primary Examiner*—Tu Ba Hoang
(74) *Attorney, Agent, or Firm*—Gary M. Cohen

(57) ABSTRACT

A heat-retractable shape memory clamp used in surgery applications is closed with a device for heating and closing heat-retractable clamps. The device includes an electronic power and control circuit which is capable of delivering different predetermined amounts of heat, each corresponding to a clamp of a given size. Settings of the electronic power and control circuit are matched to the type and size of the clamp being used so that the prongs of the clamp are closed automatically, and without the danger of accidental bone necroses. Any of a variety of heat-retractable shape memory clamps of the type generally referred to in the industry as "hot staples" may be employed with the heating device, including monocortical and bicortical bipodes, epiphysial bipodes and quadripodes, with preferred staples comprising a quantity of a nickel-titanium alloy which varies between 0.8 g and 2.8 g.

65 Claims, 1 Drawing Sheet

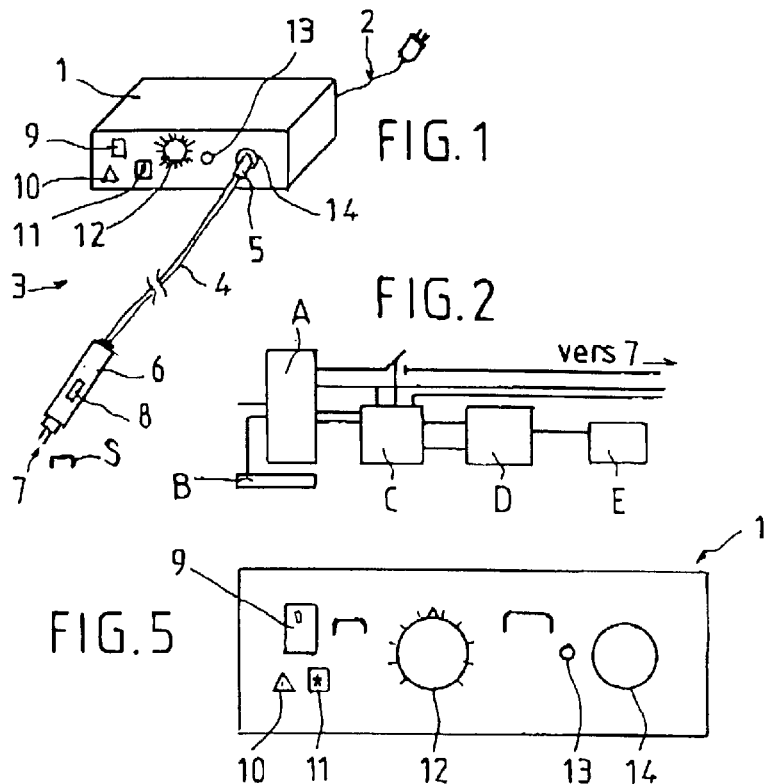
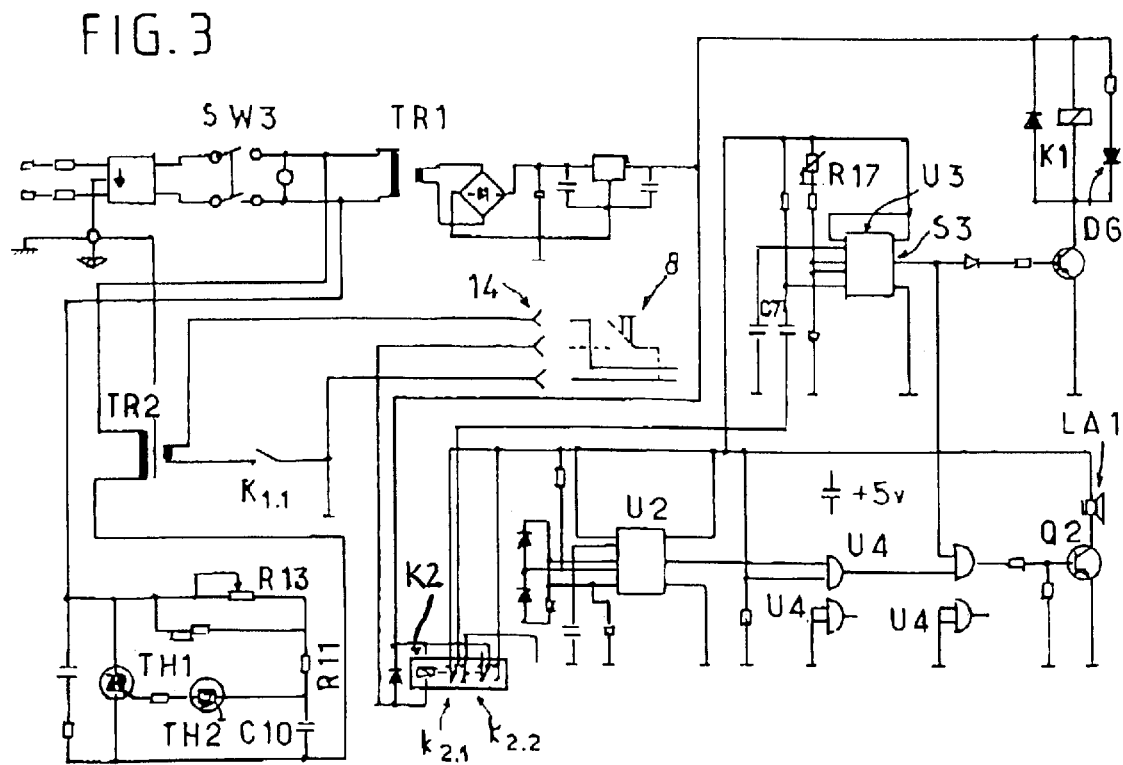

CLAMPS WITH SHAPE MEMORY

RELATED CASE

This patent application is a divisional of U.S. patent application Ser. No. 09/462,862, filed Jan. 14, 2000. Now U.S. Pat. No. 6,268,589.

BACKGROUND OF THE INVENTION

The present invention generally relates to shape memory clamps which can be closed using a device for heating and closing heat-retractable shape memory clamps, and which are particularly well suited for use in surgery applications.

More particularly, the present invention relates to shape memory clamps which can be closed using a device for heating and closing nickel/titanium alloy clamps, including clamps of the type referred to in the industry as "hot staples". Shape memory clamps are initially open at ambient temperature, for purposes of placement. A quantity of heat is then provided to close the positioned clamp and thus provide tissue support.

In practice, the ergonomic and economic standardization of surgical constraints requires such clamps to be manufactured to extremely restrictive specifications.

In this context, it is important for the device to be able to close all types of heated clamps, whether they be monocortical or bicortical, bipode or quadripode clamps, and irrespective of their section. It is also important for the device to include a reliable and effective safety system to prevent accidental bone necroses due to the heat applied by the device. It is also important for the device to have a heating cord that can be sterilized in an autoclave or disinfected in a bath.

SUMMARY OF THE INVENTION

Such goals are achieved in accordance with the present invention by providing shape memory clamps, of the type generally know as "hot staples", which can be closed using a device for heating and closing heat-retractable shape memory clamps used in surgery applications and which is generally comprised of a unit which contains an electronic power and control circuit and a heating unit.

The electronic power and control circuit is preferably comprised of a current supply, a controller and an adjustment circuit which combine to deliver several predetermined quantities of heat, each corresponding to a given size of clamp.

Primarily for purposes of safety, the adjustment circuit is configured (calculated) so that the amount of heat delivered to a given clamp does not cause the temperature of the clamp to exceed a maximum value, such as 55° C. Also for purposes of safety, the electronic circuit further includes an automatic cut-out circuit for discontinuing the application of heating current at the end of a predetermined maximum time, such as 5 seconds, and a sound signalling circuit for emitting a first sound as a signal during the application of heat to the clamp (the heating time) and a second sound which differs from the first sound as a signal that the maximum heating time has been exceeded.

The heating unit is preferably constructed as a sterilizable unit. One end of the heating unit has a plug which can be plugged into a corresponding outlet of the device and the other end of the heating unit has a sleeve which includes a pair of heating electrodes and a control switch. The sterilizable unit is fully sealed and the several elements which comprise the sterilizable unit are selected to withstand the conditions of an autoclave. In its preferred embodiment, the control switch is provided with pressure-sensitive contacts.

Any of a variety of heat-retractable shape memory clamps of the type generally referred to in the industry as "hot staples" may be employed with the above-described heating device. Preferred staples will advantageously comprise a quantity of a nickel-titanium alloy which varies between 0.8 g and 2.8 g. The electronic power and control circuit of the device includes a selection knob having settings which are matched to the type and size of the clamp being used so that the prongs of the clamp are closed both automatically and without the danger of accidental bone necroses. For example, a variety of monocortical and bicortical bipodes can be employed, with the selection knob set at one of a number of relatively low power settings (e.g., the settings 1 to 5, of 10). A variety of epiphysial bipodes and quadripodes can also be employed, with the selection knob set at one of a number of relatively high power settings (e.g., the settings 5 to 10, of 10).

The present invention shall be more readily understood from the following description, with reference to the accompanying drawings.

BRIEF DESCRIPTION OF THE DRAWINGS

FIG. 1 is an isometric view of a device for heating and closing the shape memory clamps of the present invention.

FIG. 2 is a block diagram of the electronic circuit of the device of FIG. 1.

FIG. 3 is a circuit diagram of the electronic circuit.

FIG. 4 is a cross-sectional view of the sleeve for the device.

FIG. 5 is an elevational view of the front face of the device.

DETAILED DESCRIPTION OF THE INVENTION

FIG. 1 shows a preferred embodiment device for heating the shape memory clamps of the present invention, which is generally comprised of a box (1) containing an electronic power and control circuit (to be described below), a main power supply cord (2) for connecting the box (1) to a power source (i.e., line current), and a sterilizable unit (3). The sterilizable unit (3) is formed as a linking cord (4), one end of which has a plug (5) which can be plugged into an outlet (14) of the box (1) and the other end of which has a sleeve (6) which includes two heating electrodes (7) and a control switch (8).

Referring to FIG. 5, the front face of the box (1) is equipped with a main switch (9), a luminous defect indicator light (10), a luminous "on" signal indicator light (11), a heat quantity adjustment (potentiometer) knob (12), an indicator light (13) for signalling heating of the electrodes (7) and the outlet plug (14) for receiving the sterilizable unit (3). The rear face (not shown) of the box (1) is conventionally equipped with a signalling plate and an outlet for the supply cord (2).

FIGS. 2 and 3 show the electronic power and control circuit, which is generally comprised of a current (power) supply A, an adjustment circuit B, a control circuit C and an automatic cut-out circuit D. The electronic circuit can further include an optical and sound signalling circuit E, which will be discussed below.

The current (power) supply A comprises two transformers TR1 and TR2. The primaries of the transformers TR1 and TR2 are connected to the power source. The transformer TR1 is of a type having plates resistant to short-circuits. The secondary of the transformer TR1 delivers a voltage of 12V to the control circuit C, the cut-ouit circuit D and the signalling circuit E. The transformer TR2 is a toric transformer with a screen effect. The secondary of the transformer TR2 delivers a current of 20A under 4V and is used to feed the heating electrodes (7).

The transformers TR1 and TR2 are charged by operating a main power switch (the switch SW3 of FIG. 3) which corresponds to the main switch (9) of FIG. 1. In addition to their power supplying function, the transformers TR1 and TR2 also fulfil a safety function; that being the isolation of patients and the main power supply.

The adjustment circuit B is coupled with the power supply A (phase feed) and is connected to the primary of the transformer TR2. The adjustment circuit B is generally comprised of a triac TH1, a diac TH2 and a quadrature circuit R11, C10. The triac TH1 switches from 0 to a maximum value on each cycle of the current in an extremely short period of time. This period (the "locking time") is adjusted by the diac TH2 and the potentiometer R13, which is operated responsive to the adjustment knob (12). The knob (12) is calibrated from 1 to 10, with each graduation corresponding to a predetermined amount of current for a given size of clamp.

By way of example, for a charge between electrodes of 0.1 W and 50 W and a nominal current of 1A, the respective voltage measurements on positions 1, 5 and 10 of the knob (12) are:

Position 1: 0.9V±20%;
Position 5: 1.4V±20%; and
Position 10: 2.0V±20%.

The positions 1 to 5 are primarily used for a range of monocortical and bicortical clamps of different sizes, having an alloy content of between 0.8 g and 1.7 g. The positions 5 to 10 are primarily used for a range of epiphysial and quadripode clamps having an alloy content of up to 2.8 g.

The control circuit C operates to co-ordinate the various functions of the device. Heating of the clamp is triggered by the control switch (8), which drives the relay K2. The contact $k_{2.1}$ of the relay K2 puts the capacitor C7 at zero volts. At the same time, the contact $k_{2.2}$ of the relay K2 puts the clock U3 at +12V.

Primarily for purposes of safety, the automatic cut-out circuit D operates to automatically cut off excessive heating (i.e., heating which has exceeded a predetermined period), thus limiting the amount of heat delivered to the clamp. In this way, any risk of necrosis is avoided, even if, for example, the surgeon forgets to turn off the switch (8).

The clock U3 is the main element of the circuit D. Operating times are adjusted (e.g., from 0 to 17s) by the counter (U3) and the variable resistor R17. A positive voltage is applied to the clock input so that when completed, the output (S3) of the clock has a potential and the relay K1 is released. The contact $k_{2.1}$ of the relay K2 then provides the desired timing sequence. The relay K1 is attracted and is released when the specific time has elapsed.

The optical and sound signalling circuit E includes the indicator light (11), the indicator light (13) and an acoustic signalling device LA1. The indicator (11) is illuminated to signal charging upon closure of the contacts SW3. The indicator (13), which is implemented with a LED (electroluminescent diode) D6, and the acoustic signalling device LA1 indicate the operating state for the device. To this end, the indicator (13) is illuminated when the control switch (8) is closed. At the same time, a voltage is established on the relay contact $k_{2.2}$ of the modulator U2. The modulator U2 is then activated, inducing modulation pulses in the sound signalling device LA1. The modulation pulses are sent, via gates U4, to the base of a transistor Q2 at intervals raised to 0 volts. If the control switch (8) is kept pressed when the prescribed time has elapsed, the indicator light (13) remains lit and the sound signalling device LA1 emits a continuous sound.

The electronic circuit is comprised of components which can be readily assembled by the skilled artisan.

FIG. 4 shows a sectional view of the electrode carrier sleeve. As an example, the sleeve (6) shown in FIG. 4 has a hollow cylindrical shape. However, any other ergonomic shape which will facilitate handling of the device by the surgeon can be used.

Two conductor wires (15, 16) are connected to two contact zones (8a, 8b) of a light touch switch (8). The switch (8) is in turn connected to two heating electrodes (7a, 7b). The electrodes (7a, 7b) are kept parallel at the extremity of the sleeve (6), and are conventionally insulated by a non-conducting bush (17). A central conductor (18) is provided to ensure proper grounding.

The unit including the linking cord (4), the sleeve (6) and the plug (5) is made of materials which can be sterilized in an autoclave, withstanding temperatures of up to 134° C. The unit further includes a gasket (19) adjacent to the linking cord (4) to further allow for sterilization of the unit by immersion, if desired. A reinforcement piece (20) is provided at the outlet for the linking cord (4) to avoid kinking and to protect the conductor wires (15, 16, 18).

In use, the placement of a clamp by the surgeon proceeds as follows. The bone fragments to be joined are appropriately prepared and positioned. Drilling guides are then placed on both sides of the fracture and holes for receiving the clamps are drilled. The clamps are then placed, one after the other, in the drilled holes. The heating device is then charged, by turning on the main switch (9), and the position for the adjustment knob (12) is selected (according to the clamp which is being used). The sleeve of the device is then pressed on the clamp which is to be closed, and heating is initiated by depressing the switch (8) once the proper current has been established. An intermittent sound (signal) is then made by the device.

The electronic power and control circuit then operates to automatically determine and regulate the suitable amount of heat which is to be applied to each clamp, responsive to the position selected for the adjustment knob (12). The applied current can be interrupted by the surgeon on closing of the clamp, or in default (e.g., at the end of five seconds), by the automatic cut-out circuit D. A continuous sound (signal) is then made by the device to warn the surgeon.

The above-described heating device provides a variety of improvements. For example, any type of heated clamp (i.e., the clamp S shown in FIG. 1) can be used. To this end, the spacing of the electrodes (7a, 7b) is set (e.g., at 15 mm) to allow the dorsal parts of the smaller and average-sized clamps, such as monocortical and bicortical bipodes having an alloy content of from 0.8 g to 1.7 g, to be heated (from the back) in a single application. For the larger clamps, such as epiphysial bipodes and quadripode clamps having an alloy content of up to 2.8 g, dorsal parts of the clamp at two opposing angles are first heated (from the back), followed by the heating (from the back) of remaining dorsal parts of the clamp, at opposing angles, which has the effect of successively folding the prongs of the clamp. These operations c an be repeated, as needed, to effectuate plural impulses. In any event, the amount of heat delivered to the clamp is automatically limited. In particular, the amount of heat delivered to the clamp is limited so that the temperature reached by the alloy of the clamp is limited to 55° C. The period for applying heat to the clamp is also automatically limited. The sleeve is totally impervious to liquids, and there is no risk of explosion because the electrical contacts used do not create any electric arcs.

As previously indicated, the above-described heating device can be used with any of a variety of heat-retractable shape memory clamps S used in surgery, which are generally referred to in the industry as "hot staples". However, the above-described heating device is most favorably used with staples which are specially designed to be closed using the above-described heating device. Such staples will preferably comprise a quantity of a nickel-titanium alloy which varies between 0.8 g and 2.8 g.

A typical monocortical bipode can have a size of 11 mm×8 mm, with a section of 1.0 mm×1.0 mm, and is preferably closed using a device with the knob (12) set to a position from 1 to 5, operating at one impulse. Alternative monocortical bipodes can have sizes of 11 mm×10 mm, 13 mm×10 mm and 15 mm×1 mm, each with a section of 1.5 mm×1.5 mm, and which are in each case preferably closed using a device with the knob (12) set to a position from 1 to 5, operating at two impulses.

Typical bicortical bipodes can have sizes of 11 mm×15 mm×13 mm, 11 mm×17 mm×15 mm and 11 mm×19 mm×17 mm, each with a section of 1.5 mm×1.5 mm, and which are in each case preferably closed using a device with the knob (12) set to a position from 1 to 5, operating at two impulses.

Typical epiphysial bipodes can have sizes of 20 mm×20 mm, 25 mm×22 mm and 30 mm×30 mm, each with a section of 3.0 mm×2.0 mm, and which are in each case preferably closed using a device with the knob (12) set to a position from 5 to 10, operating at three impulses.

Typical quadripodes can have an entreax (span) of 9 mm or 15 mm, combined with prongs having a length of 6 mm, or an entreax (span) of 15 mm, combined with prongs having a length of 8 mm or 10 mm, in each case having a section of 1.5 mm×1.2 mm. As previously indicated, such quadripodes are advantageously closed using a device with the knob (12) set to a position from 5 to 10.

The quadripodes are advantageously used to increase the stability of a number of osteosynthesis, having the advantages of a miniplaque, without the use of screws. The use of quadripodes is particularly recommended when secondary displacements are of concern because the stability of the osteosynthesis is ensured in all directions. Quadripodes are also well suited to foot surgery indications, as well as maxilo-facial surgery (e.g., mandibular osteosynthesis in the symphysis and para-symphysis region, and osteosynthesis of Lefort 1 type osteotomies) and cranioplasty.

It will be understood that various changes in the details, materials and arrangement of parts which have been herein described and illustrated in order to explain the nature of this invention may be made by those skilled in the art within the principle and scope of the invention as expressed in the following claims.

What is claimed is:

1. A heat-retractable shape memory clamp used in surgery applications which is closed with a device for heating and closing the heat-retractable shape memory clamp, wherein the heat-retractable shape memory clamp comprises a quantity of a nickel-titanium alloy which varies between 0.8 g and 2.8 g, wherein the device includes a unit containing an electronic power and control circuit supplied with line current which is coupled with a heating unit, wherein the electronic power and control circuit comprises a current supplying circuit, a system controller and an adjustment circuit, and wherein the electronic power and control circuit operates to automatically deliver one of a plurality of different and predetermined quantities of heat to the clamp using the heating unit.

2. The clamp of claim 1 wherein each of the plurality of different and predetermined quantities of heat produced by the device is selected to correspond to a different and predetermined configuration for the clamp.

3. The clamp of claim 2 wherein the device develops a lower series of settings including predetermined quantities of heat which are lower than an upper series of settings including predetermined quantities of heat which are higher than the predetermined quantities of heat corresponding to the lower series of settings.

4. The clamp of claim 3 wherein the lower series of settings and the upper series of settings correspond to different and predetermined configurations for the clamp.

5. The clamp of claim 3 wherein the clamp is a monocortical bipode having an alloy content of from 0.8 g to 1.7 g.

6. The clamp of claim 5 wherein the monocortical bipode has a size of 11 mm×8 mm, with a section of 1.0 mm×1.0 mm.

7. The clamp of claim 6 wherein the clamp is closed using a device set to one of the lower series of settings.

8. The clamp of claim 5 wherein the monocortical bipode has a size selected from the group of clamp sizes consisting of 11 mm×10 mm, 13 mm×10 mm and 15 mm×10 mm, with a section of 1.5 mm×1.5 mm.

9. The clamp of claim 8 wherein the clamp is closed using a device set to one of the lower series of settings.

10. The clamp of claim 3 wherein the clamp is a bicortical bipode having an alloy content of from 0.8 g to 1.7 g.

11. The clamp of claim 10 wherein the bicortical bipode has a size selected from the group of clamp sizes consisting of 11 mm×15 mm×13 mm, 11 mm×17 mm×15 mm and 11 mm×19 mm×17 mm, with a section of 1.5 mm×1.5 mm.

12. The clamp of claim 11 wherein the clamp is closed using a device set to one of the lower series of settings.

13. The clamp of claim 3 wherein the clamp is an epiphysial bipode having an alloy content of up to 2.8 g.

14. The clamp of claim 13 wherein the epiphysial bipode has a size selected from the group of clamp sizes consisting of 20 mm×20 mm, 25 mm×22 mm and 30 mm×30 mm, with a section of 3.0 mm×2.0 mm.

15. The clamp of claim 14 wherein the clamp is closed using a device set to one of the upper series of settings.

16. The clamp of claim 3 wherein the clamp is a quadripode having an alloy content of up to 2.8 g.

17. The clamp of claim 16 wherein the quadripode has a span of 9 mm, and prongs having a length of 6 mm, with a section of 1.5 mm×1.2 mm.

18. The clamp of claim 16 wherein the quadripode has a span of 15 mm, and prongs having a length of 6 mm, with a section of 1.5 mm×1.2 mm.

19. The clamp of claim 16 wherein the quadripode has a span of 15 mm, and prongs having a length of 8 mm, with a section of 1.5 mm×1.2 mm.

20. The clamp of claim 16 wherein the quadripode has a span of 15 mm, and prongs having a length of 10 mm, with a section of 1.5 mm×1.2 mm.

21. The clamp of claim 16 wherein the clamp is closed using a device set to one of the upper series of settings.

22. The clamp of claim 3 wherein the clamp has plural prongs located at opposing angles of the clamp, and wherein the prongs of the clamp at two opposing angles are closed in a first heating operation, and wherein the prongs of the clamp at another two opposing angles are closed in a second heating operation, to successively fold the prongs of the clamp.

23. The clamp of claim 1 wherein the electronic power and control circuit is configured to automatically limit the amount of heat delivered to the clamp so that the temperature generated in the clamp does not exceed a maximum value.

24. The clamp of claim 23 wherein the maximum value for the temperature is 55° C.

25. The clamp of claim 1 wherein the electronic power and control circuit further includes an automatic cut-out circuit coupled with the adjustment circuit, and wherein the cut-out circuit automatically cuts the heating current applied to the clamp at the end of a predetermined maximum time.

26. The clamp of claim 25 wherein the maximum time is limited to 5 seconds.

27. The clamp of claim 1 wherein the electronic power and control circuit automatically limits the voltage supplied to the heating unit and the amount of time that the voltage is supplied to the heating unit.

28. The clamp of claim 1 wherein the electronic power and control circuit further includes a sound signaling circuit, and wherein the sound signaling circuit emits a first sound signal during heating of the clamp and a second sound signal different from the first sound signal for heating of the clamp which exceeds the maximum heating time.

29. The clamp of claim 1 wherein the heating unit includes a linking cord which is coupled with a pair of heating electrodes, wherein the heating electrodes are separated by a spacing of approximately 15 mm.

30. A heat-retractable shape memory clamp used in surgery applications which is comprised of a quantity of a nickel-titanium alloy from 0.8 g to 2.8 g, wherein the clamp is matched to one of a plurality of settings of a device for heating and closing the heat-retractable shape memory clamp, wherein the device includes an electronic power and control circuit supplied with line current which is coupled with a heating unit, wherein the electronic power and control circuit comprises a current supplying circuit, a system controller and an adjustment circuit, and wherein the electronic power and control circuit operates to automatically deliver to the clamp, using the heating unit, a predetermined quantity of heat which is determined by said one of the plurality of settings of the device which is matched to the clamp.

31. The clamp of claim 30 wherein the clamp is a monocortical bipode having an alloy content of from 0.8 g to 1.7 g.

32. The clamp of claim 31 wherein the monocortical bipode has a size of 11 mm×8 mm, with a section of 1.0 mm×1.0 mm.

33. The clamp of claim 31 wherein the monocortical bipode has a size selected from the group of clamp sizes consisting of 11 mm×10 mm, 13 mm×10 mm and 15 mm×10 mm, with a section of 1.5 mm×1.5 mm.

34. The clamp of claim 30 wherein the clamp is a bicortical bipode having an alloy content of from 0.8 g to 1.7 g.

35. The clamp of claim 34 wherein the bicortical bipode has a size selected from the group of clamp sizes consisting of 11 mm×15 mm×13 mm, 11 mm×17 mm×15 mm and 11 mm×19 mm×17 mm, with a section of 1.5 mm×1.5 mm.

36. The clamp of claim 30 wherein the clamp is an epiphysial bipode having an alloy content of up to 2.8 g.

37. The clamp of claim 36 wherein the epiphysial bipode has a size selected from the group of clamp sizes consisting of 20 mm×20 mm, 25 mm×22 mm and 30 mm×30 mm, with a section of 3.0 mm×2.0 mm.

38. The clamp of claim 30 wherein the clamp is a quadripode having an alloy content of up to 2.8 g.

39. The clamp of claim 38 wherein the quadripode has a span of 9 mm, and prongs having a length of 6 mm, with a section of 1.5 mm×1.2 mm.

40. The clamp of claim 38 wherein the quadripode has a span of 15 mm, and prongs having a length of 6 mm, with a section of 1.5 mm×1.2 mm.

41. The clamp of claim 38 wherein the quadripode has a span of 15 mm, and prongs having a length of 8 mm, with a section of 1.5 mm×1.2 mm.

42. The clamp of claim 38 wherein the quadripode has a span of 15 mm, and prongs having a length of 10 mm, with a section of 1.5 mm×1.2 mm.

43. The device of claim 30 wherein the electronic power and control circuit develops a plurality of different and predetermined quantities of heat corresponding to different and predetermined configurations for the clamp.

44. The clamp of claim 43 wherein the device develops a lower series of settings including predetermined quantities of heat which are lower than an upper series of settings including predetermined quantities of heat which are higher than the predetermined quantities of heat corresponding to the lower series of settings.

45. The clamp of claim 44 wherein the lower series of settings and the upper series of settings correspond to different and predetermined configurations for the clamp.

46. The clamp of claim 44 wherein the clamp is a monocortical bipode, and wherein the clamp is closed using a device set to one of the lower series of settings.

47. The clamp of claim 44 wherein the clamp is a bicortical bipode, and wherein the clamp is closed using a device set to one of the lower series of settings.

48. The clamp of claim 44 wherein the clamp is an epiphysial bipode, and wherein the clamp is closed using a device set to one of the upper series of settings.

49. The clamp of claim 44 wherein the clamp is a quadripode, and wherein the clamp is closed using a device set to one of the upper series of settings.

50. The clamp of claim 49 wherein the clamp has plural prongs located at opposing angles of the clamp, and wherein the prongs of the clamp at two opposing angles are closed in a first heating operation, and wherein the prongs of the clamp at another two opposing angles are closed in a second heating operation, to successively fold the prongs of the clamp.

51. A method for closing a heat-retractable shape memory clamp in a surgery application using a device for heating and closing the heat-retractable shape memory clamp, wherein the device includes an electronic power and control circuit supplied with line current which is coupled with a heating unit, and wherein the method comprises the steps of:

selecting the clamp to be used in the surgery application, wherein the selected clamp is comprised of a quantity of a nickel-titanium alloy from 0.8 g to 2.8 g, and wherein the selected clamp has a defined configuration;

selecting one of a plurality of settings for the electronic power and control circuit of the device, wherein the selected setting corresponds to the defined configuration of the selected clamp; and automatically delivering to the clamp, using the heating unit, a predetermined quantity of heat produced responsive to the electronic power and control circuit and determined by the selected setting.

52. The method of claim 51 which further includes the step of providing a lower series of settings for the device which includes predetermined quantities of heat lower than an upper series of settings for the device which includes predetermined quantities of heat higher than the predetermined quantities of heat corresponding to the lower series of settings.

53. The method of claim 52 wherein the lower series of settings and the upper series of settings correspond to different and predetermined configurations for the clamp.

54. The method of claim 52 wherein the clamp is a monocortical bipode having an alloy content of from 0.8 g to 1.7 g, and wherein the method further includes the step of closing the clamp using a device set to one of the lower series of settings.

55. The method of claim 52 wherein the clamp is a bicortical bipode having an alloy content of from 0.8 g to 1.7 g, and wherein the method further includes the step of closing the clamp using a device set to one of the lower series of settings.

56. The method of claim 52 wherein the clamp is an epiphysial bipode having an alloy content of up to 2.8 g, and wherein the method further includes the step of closing the clamp using a device set to one of the upper series of settings.

57. The method of claim 52 wherein the clamp is a quadripode having an alloy content of up to 2.8 g, and wherein the method further includes the step of closing the clamp using a device set to one of the upper series of settings.

58. The method of claim 57 wherein the clamp has plural prongs located at opposing angles of the clamp, and wherein the method further includes the steps of first closing prongs of the clamp at two opposing angles in a first heating operation, and then closing other prongs of the clamp at another two opposing angles in a second heating operation, successively folding the prongs of the clamp.

59. The method of claim 51 which further includes the step of applying plural heating impulses to the clamp during the closing of the clamp.

60. The method of claim 51 which further includes the step of automatically limiting the amount of heat delivered to the clamp, using the electronic power and control circuit, so that the temperature generated in the clamp does not exceed a maximum value.

61. The method of claim 60 wherein the maximum value for the temperature is 55° C.

62. The method of claim 51 which further includes the step of automatically cutting off heating current applied to the clamp at the end of a predetermined maximum time, using an automatic cut-out circuit coupled with the electronic power and control circuit.

63. The method of claim 62 wherein the maximum time is limited to 5 seconds.

64. The method of claim 51 which further includes the step of automatically limiting voltage supplied to the heating unit and the amount of time that the voltage is supplied to the heating unit, using the electronic power and control circuit.

65. The method of claim 51 wherein the electronic power and control circuit further includes a sound signaling circuit, and wherein the method further includes the steps of emitting a first sound signal, using the sound signaling circuit, during heating of the clamp and emitting a second sound signal different from the first sound signal, using the sound signaling circuit, for heating of the clamp which exceeds a maximum heating time.

* * * * *